(12) United States Patent
Jung et al.

(10) Patent No.: US 9,354,222 B2
(45) Date of Patent: May 31, 2016

(54) DIAGNOSTIC METHOD OF CARDIOVASCULAR DISEASE

(71) Applicant: KOREA INSTITUTE OF SCIENCE AND TECHNOLOGY, Seoul (KR)

(72) Inventors: Byung Hwa Jung, Seoul (KR); Jong Min Choi, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 88 days.

(21) Appl. No.: 14/185,300

(22) Filed: Feb. 20, 2014

(65) Prior Publication Data

US 2015/0198582 A1 Jul. 16, 2015

(30) Foreign Application Priority Data

Jan. 14, 2014 (KR) .................. 10-2014-0004510

(51) Int. Cl.
*G01N 33/49* (2006.01)
*G01N 30/72* (2006.01)
*G01N 33/92* (2006.01)

(52) U.S. Cl.
CPC ............ *G01N 33/492* (2013.01); *G01N 33/92* (2013.01); *G01N 30/72* (2013.01); *G01N 2800/324* (2013.01); *Y10T 436/24* (2015.01)

(58) Field of Classification Search
CPC ....... G01N 33/48; G01N 33/49; G01N 33/92; G01N 30/72; G01N 2800/00; G01N 2800/32; G01N 2800/324; G01N 2800/50; G01N 2800/52; G01N 2800/56; Y10T 436/24
USPC .......... 436/63, 71, 161, 173; 422/430; 435/29
See application file for complete search history.

(56) References Cited

U.S. PATENT DOCUMENTS

| | | | |
|---|---|---|---|
| 2010/0021956 A1* | 1/2010 | Shearer et al. .................. | 435/29 |
| 2011/0045514 A1 | 2/2011 | Muntendam et al. | |
| 2011/0137131 A1* | 6/2011 | Adourian et al. ............. | 600/300 |
| 2011/0287449 A1 | 11/2011 | Hazen et al. | |
| 2011/0317131 A1 | 12/2011 | Miyazaki | |
| 2013/0023054 A1* | 1/2013 | Meikle .................. | G01N 33/92 436/71 |
| 2013/0045217 A1 | 2/2013 | Laaksonen et al. | |
| 2014/0100128 A1* | 4/2014 | Narain et al. ..................... | 506/9 |

FOREIGN PATENT DOCUMENTS

| | | |
|---|---|---|
| KR | 10-1040321 | 6/2011 |
| KR | 10-1051470 | 7/2011 |
| WO | 2009036376 A1 | 3/2009 |

OTHER PUBLICATIONS

Lee et al., Lysophosphatidylcholine, Oxidized Low-Density Lipoprotein and Cardiovascular Disease in Korean Hemodialysis Patients: Analysis at 5 Years of Follow-up, J Korean Med Sci, 2013, pp. 268-273, vol. 28, Original Article, Korea.
G. D. Lewis et al., "Metabolite profiling of blood from individuals undergoing planned myocardial infarction reveals early markers of myocardial injury," *The Journal of Clinical Investigation*, vol. 118, No. 10, Oct. 2008, pp. 3503-3512.
M. G. Barderas et al., "Metabolomic Profiling for Identification of Novel Potential Biomarkers in Cardiovascular Diseases," *Journal of Biomedicine and Biotechnology*, vol. 2011, Art. No. 790132, 2011, 9 pages.
P. Jiang et al., "Potential biomarkers in the urine of myocardial infarction rats: a metabolomic method and its application," *Molecular Biosystems*, vol. 7, 2011, pp. 824-831.
S. H. Shah et al., "Metabolomic Profiling for the Identification of Novel Biomarkers and Mechanisms Related to Common Cardiovascular Diseases: Form and Function," *Circulation*, vol. 126, 2012, pp. 1110-1120 and Cover Page.
G. Tan et al., "Hydrophilic interaction and reversed-phase ultraperformance liquid chromatography TOF-MS for serum metabonomic analysis of myocardial infarction in rats and its applications," *Molecular Systems*, vol. 8, 2012, pp. 548-556.

* cited by examiner

*Primary Examiner* — Maureen Wallenhorst
(74) *Attorney, Agent, or Firm* — Goldilocks ZONE IP LAW

(57) ABSTRACT

Biological metabolites LysoPC (18:0), LysoPC (20:3), fatty acid (16:1), fatty acid (18:0), fatty acid (18:1), fatty acid (18:2) and fatty acid (22:6) according to the present disclosure allow for simple and accurate diagnosis of a cardiovascular disease since their level in the blood of a subject increases or decreases if the subject has a cardiovascular disease such as myocardial infarction or angina. In addition, whereas the existing biomarkers can diagnose only whether myocardial infarction occurs or not, the biological metabolites according to the present disclosure can diagnose not only myocardial infarction but also unstable angina occurring prior to the onset of myocardial infarction stage by stage.

2 Claims, 11 Drawing Sheets

(c) MS spectrum in negative mode

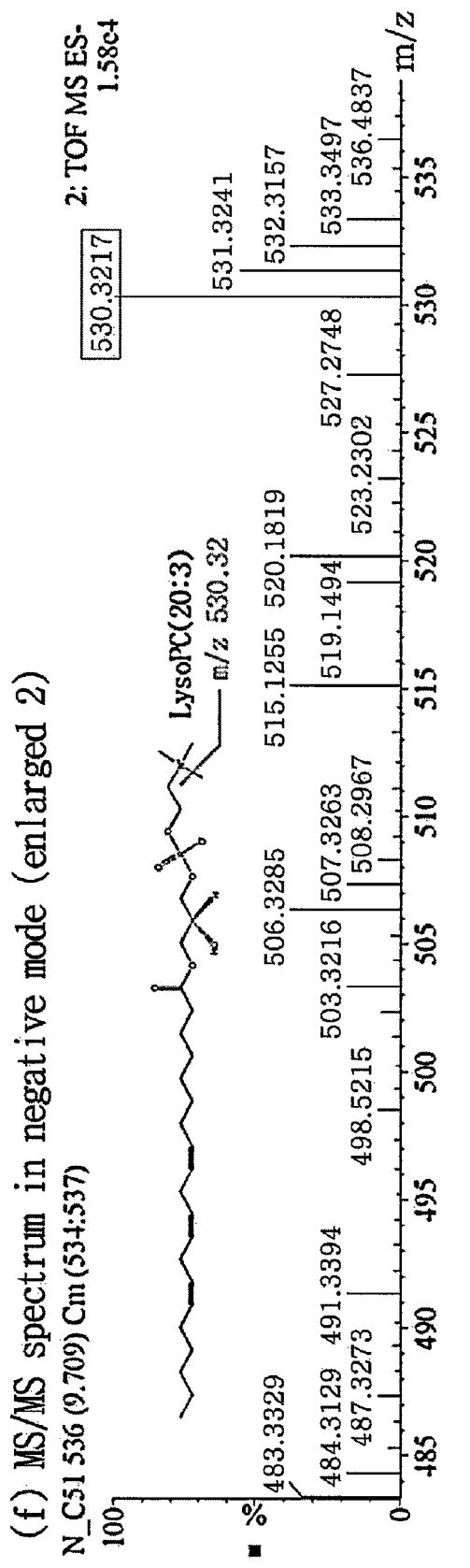

DIAGNOSTIC METHOD OF CARDIOVASCULAR DISEASE

CROSS-REFERENCE TO RELATED APPLICATION

This application claims priority to Korean Patent Application No. 10-2014-0004510, filed on Jan. 14, 2014, and all the benefits accruing therefrom under 35 U.S.C. §119, the contents of which in its entirety are herein incorporated by reference.

BACKGROUND

1. Field

The present disclosure relates to a method and a kit for diagnosing a cardiovascular disease.

2. Description of the Related Art

Cardiovascular disease (CVD) is the leading cause of deaths worldwide. According to a report by the World Health Organization (WHO), it is estimated that 23.6 million people will die from cardiovascular diseases annually by 2030. Among them, myocardial infarction, which is a fatal disease and the leading cause of sudden deaths in adults, is gradually increasing. This disease is characterized by imbalance in oxygen supply to heart muscles due to obstruction of coronary arteries and irreversible heart muscle cell damage. Unlike stable angina wherein the lesion is formed stably and which can be predicted and diagnosed with repetitive and characteristic chest pain, myocardial infarction is accompanied by thrombotic occlusion of coronary arteries caused by sudden rupture of vulnerable plaques. The detection of the vulnerable plaques is conventionally possible only with an invasive manner, for example, using intravascular ultrasound (IVUS) and early diagnosis is difficult because of the absence of biomarkers allowing for prediction and diagnosis before the onset of the disease.

The coronary artery disease leads to the symptom of angina. Angina can be classified into stable angina and unstable angina. Especially, unstable angina is a very dangerous disease unlike stable angina since the risk of disruption of atherosclerotic plaques is high even when the lesion size is small. Therefore, development of a biomarker that can detect unstable angina which occurs prior to myocardial infarction is urgently necessary for early diagnosis of myocardial infarction. Such a biomarker will be clinically very useful for early diagnosis of preonset of myocardial infarction.

At present, glutamic oxaloacetic transaminase (GOT), lactate dehydrogenase (LDH), creatine kinase-MB (CK-MB), troponin I, troponin T, C-reactive protein (CRP) and B-type natriuretic peptide (BNP) are used as biomarkers for diagnosis of cardiovascular disease or heart failure. However, these are not biomarkers specific for myocardial infarction or they are detectable only after the onset of myocardial infarction. In addition, no diagnostic biomarker using small-molecule metabolites found in the blood is known yet. Accordingly, there is a need of a marker specific for myocardial infarction and capable of predicting lesion prior to the onset of myocardial infarction and a method for diagnosing a cardiovascular disease using same.

PATENT DOCUMENTS

Korean Patent Registration Publication No. 10-1051470
Korean Patent Registration Publication No. 10-1040321
US Patent Publication No. 2011-0137131

Non-Patent Documents

Lewis G D, Wei R, Liu E, Yang E, Shi X, Martinovic M, Farrell L, Asnani A, Cyrille M, Ramanathan A, Shaham O, Berriz G, Lowry P A, Palacios I F, Taş an M, Roth F P, Min J, Baumgartner C, Keshishian H, Addona T, Mootha V K, Rosenzweig A, Carr S A, Fifer M A, Sabatine M S, Gerszten R E. Metabolite profiling of blood from individuals undergoing planned myocardial infarction reveals early markers of myocardial injury. *J Clin Invest.* 2008; 118(10): 3503-12.

Shah S H, Kraus W E, Newgard C B. Metabolomic Profiling for the Identification of Novel Biomarkers and Mechanisms Related to Common Cardiovascular Diseases. *Circulation.* 2012; 126(9): 1110-20.

Jiang P, Dai W, Yan S, Chen Z, Xu R, Ding J, Xiang L, Wang S, Liu R, Zhang W. Potential biomarkers in the urine of myocardial infarction rats: a metabolomic method and its application. *Mol Biosyst.* 2011; 7(3): 824-31.

Tan G, Lou Z, Liao W, Dong X, Zhu Z, Li W, Chai Y. Hydrophilic interaction and reversed-phase ultraperformance liquid chromatography TOF-MS for serum metabolomic analysis of myocardial infarction in rats and its applications. *Mol Biosyst.* 2012; 8(2): 548-56.

Barderas M G, Laborde C M, Posada M, de la Cuesta F, Zubiri I, Vivanco F, Alvarez-Llamas G. Metabolomic Profiling for Identification of Novel Potential Biomarkers in Cardiovascular Diseases. *J Biomed Biotechnol.* 2011; 2011: 790132.

SUMMARY

The present disclosure is directed to providing a biological metabolite serving as a biomarker for diagnosis of a cardiovascular disease and a method for diagnosing a cardiovascular disease based on qualitative and quantitative analysis of the biological metabolite in blood. Also, the present disclosure is directed to providing a kit for diagnosing a cardiovascular disease, including a measuring unit measuring the biological metabolite.

In one aspect, the present disclosure provides a method for diagnosing a cardiovascular disease, including: measuring the level of one or more biological metabolite selected from lysophosphatidylcholine (LysoPC) (18:0), LysoPC (20:3), fatty acid (16:1) (palmitelaidic acid), fatty acid (18:0) (stearic acid), fatty acid (18:1) (oleic acid), fatty acid (18:2) (linoleic acid) and fatty acid (22:6) (docosahexaenoic acid) in blood taken from a subject; and comparing the level of the biological metabolite in the blood with the level of the biological metabolite in blood from a normal control group.

In another aspect, the present disclosure provides a kit for diagnosing a cardiovascular disease, including a measuring unit measuring one or more biological metabolite selected from lysophosphatidylcholine (LysoPC) (18:0), LysoPC (20:3), fatty acid (16:1) (palmitelaidic acid), fatty acid (18:0) (stearic acid), fatty acid (18:1) (oleic acid), fatty acid (18:2) (linoleic acid) and fatty acid (22:6) (docosahexaenoic acid).

Since the biological metabolites according to the present disclosure are not lipoproteins based on proteins but lipids, they can be easily analyzed in blood. In particular, since the level of LysoPC (18:0), LysoPC (20:3), fatty acid (16:1), fatty acid (18:0), fatty acid (18:1), fatty acid (18:2) and fatty acid (22:6) in blood increases or decreases when a subject has a cardiovascular disease such as myocardial infarction and angina, the cardiovascular disease can be diagnosed simply and accurately by comparing their level in blood. In addition, whereas the existing biomarkers can diagnose only whether myocardial infarction occurs or not, the biological metabolites according to the present disclosure can diagnose not only myocardial infarction but also unstable angina occurring prior to the onset of myocardial infarction. Accordingly, it is useful for early diagnosis of myocardial infarction from the preonset of the myocardial infarction by stages.

Accordingly, use of the biological metabolites according to the present disclosure allows for diagnosis of myocardial infarction and unstable angina and prediction of therapeutic effect and successful prevention of the diseases through simple blood testing.

BRIEF DESCRIPTION OF THE DRAWINGS

The above and other aspects, features and advantages of the disclosed exemplary embodiments will be more apparent from the following detailed description taken in conjunction with the accompanying drawings in which:

FIGS. 8A to 8D compare the MS spectrum of LysoPC (20:3) among metabolite biomarkers according to an exemplary embodiment of the present disclosure obtained in Test Example 1 with a theoretical spectrum pattern available from an online database [The spectra (c), (d), (e) and (f) of FIGS. 8A to 8D were obtained in the negative ionization mode. The spectrum pattern of LysoPC (20:3) obtained from the database is shown in (e)-(f) of FIGS. 8C and 8D together with the structure of LysoPC (20:3).].

DETAILED DESCRIPTION

Figure 1:
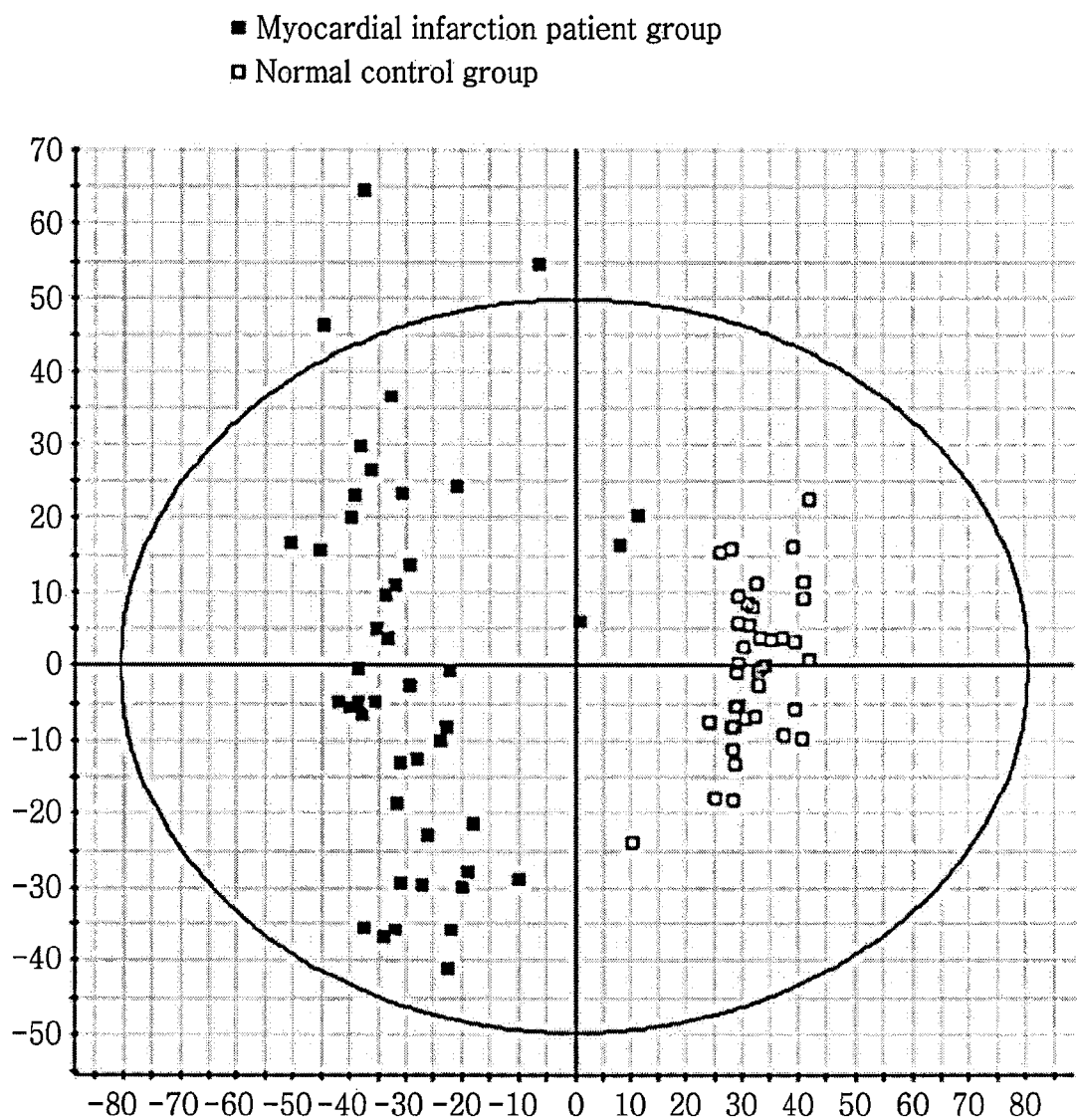
FIG. 1 shows a result of multivariate analysis performed by the orthogonal partial least square-discriminant analysis (OPLS-DA) method based on the chromatographic result of biological metabolites in plasma samples of a normal control group and a myocardial infarction patient group.
Figure 2:
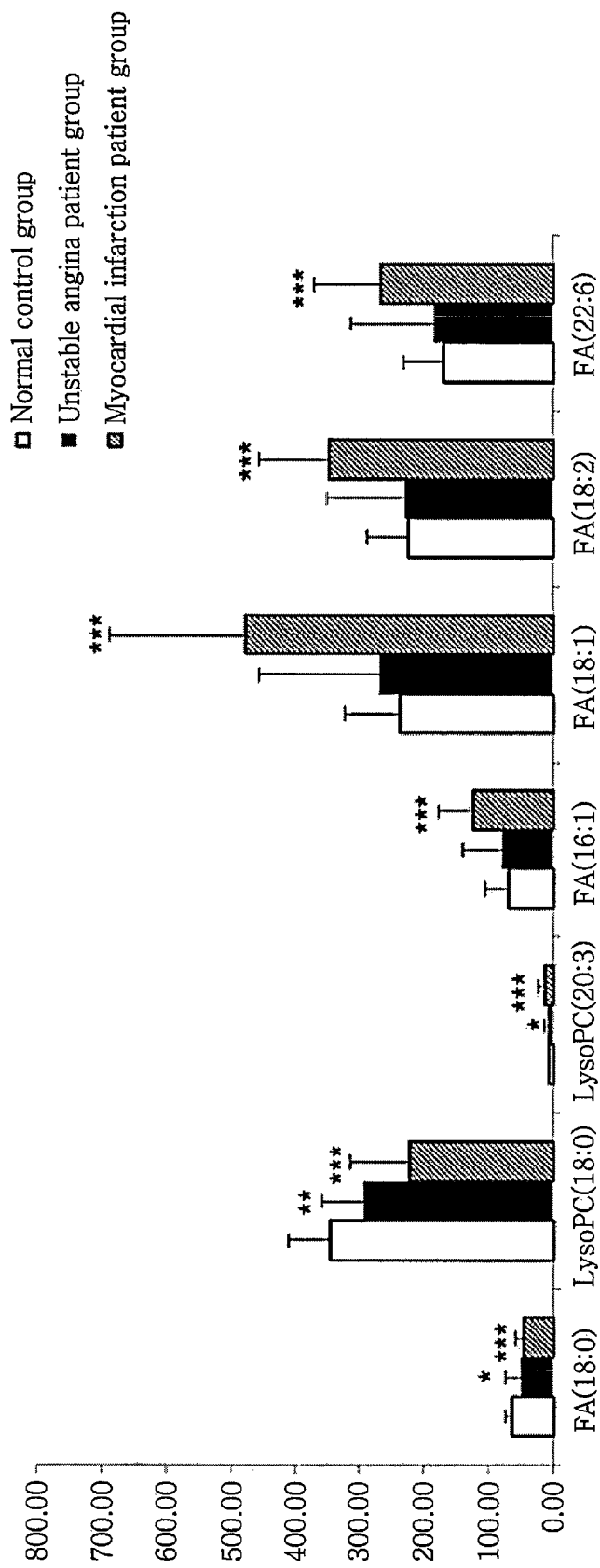
FIG. 2 compares the relative amount of metabolite biomarkers according to an exemplary embodiment of the present disclosure in blood in a normal control group and unstable angina and myocardial infarction patient groups (FA: fatty acid, LysoPC: lysophosphatidylcholine)
Figure 3:
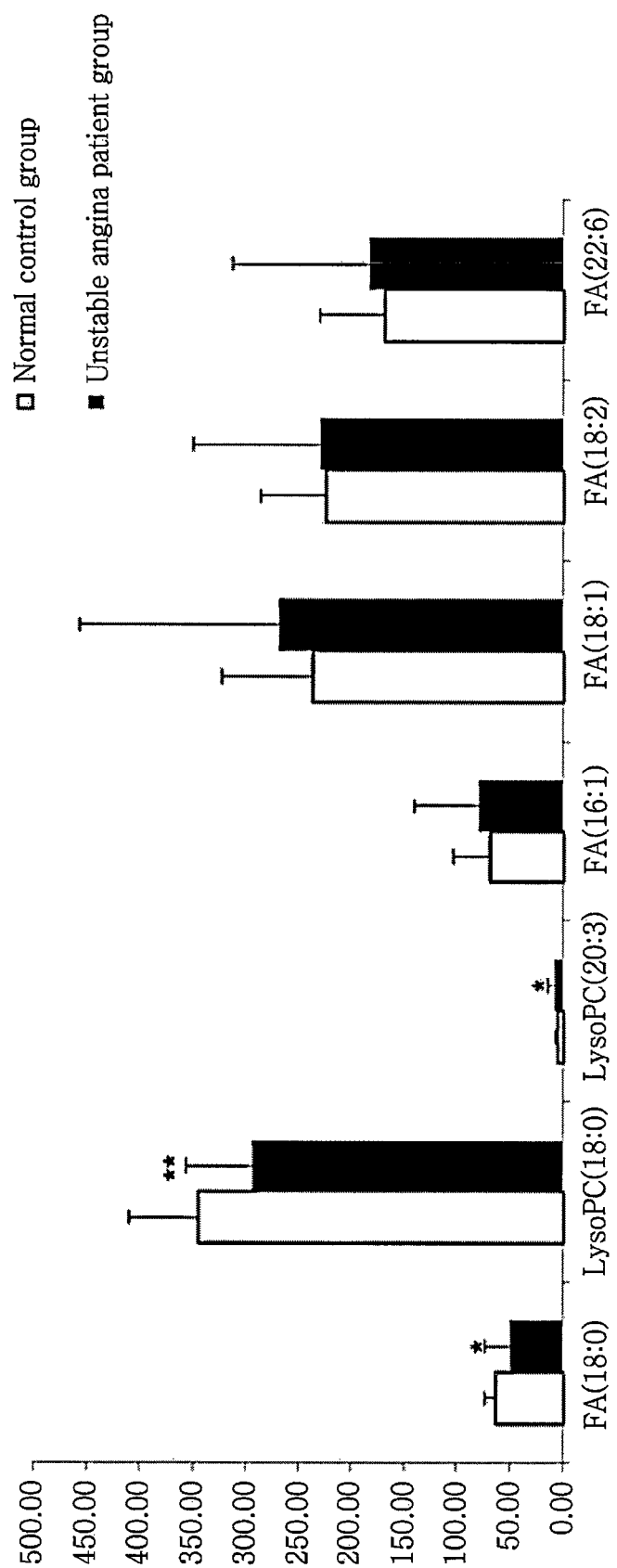
FIG. 3 compares the relative amount of metabolite biomarkers according to an exemplary embodiment of the present disclosure in blood in a normal control group and an unstable angina patient group.
Figure 4:
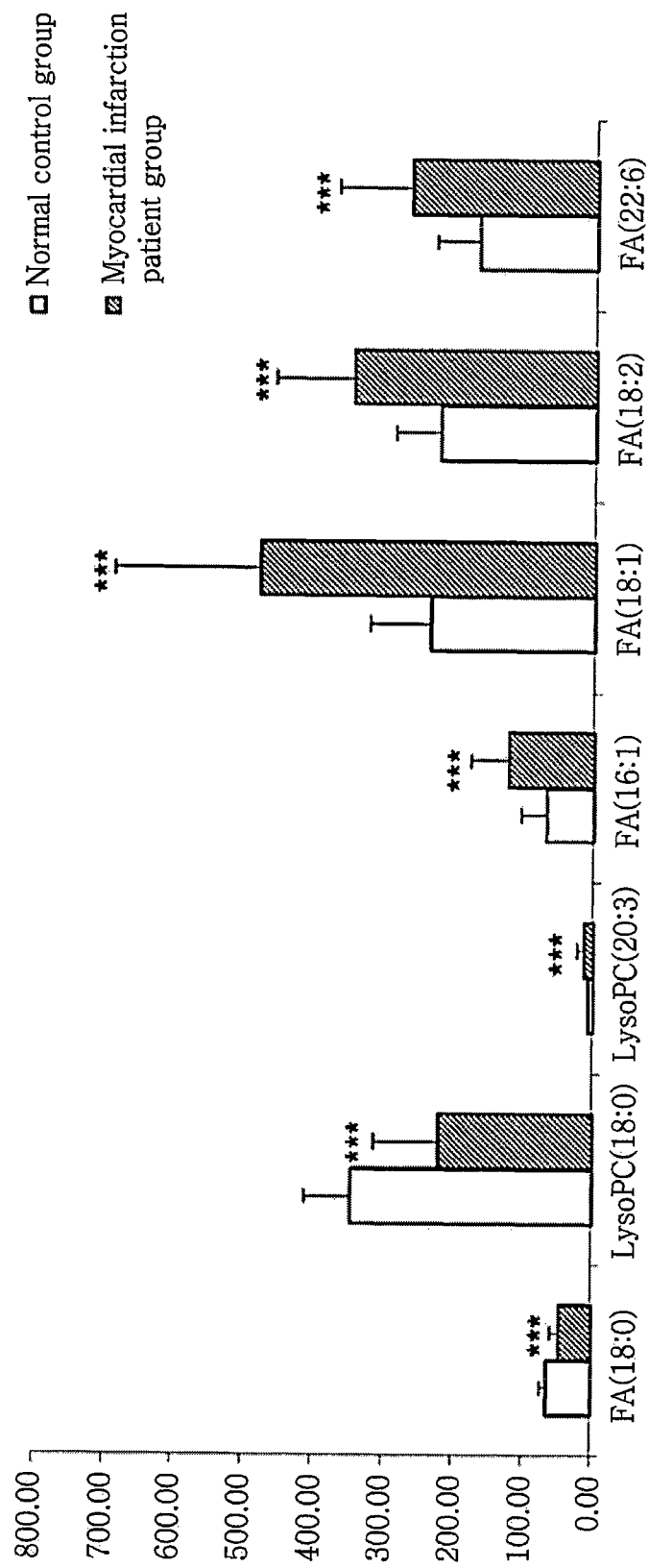
FIG. 4 compares the relative amount of metabolite biomarkers according to an exemplary embodiment of the present disclosure in blood in a normal control group and a myocardial infarction patient group.
Figure 5:
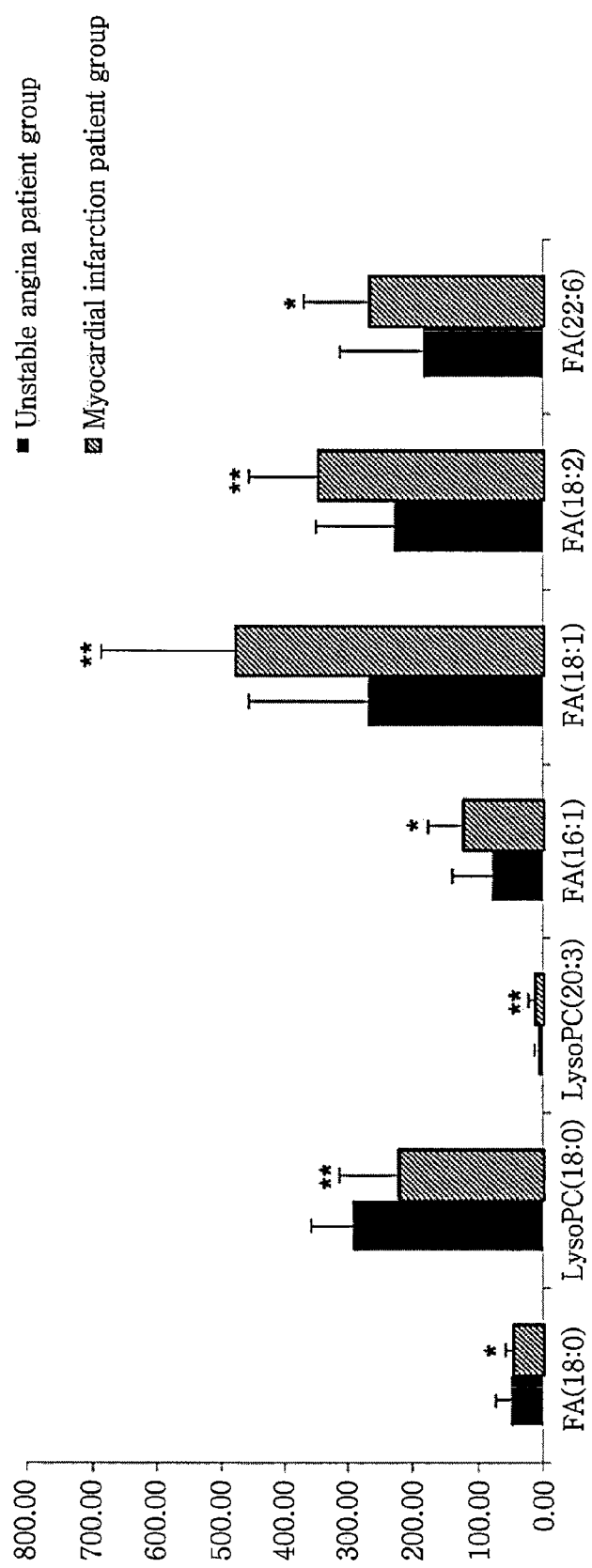
FIG. 5 compares the relative amount of metabolite biomarkers according to an exemplary embodiment of the present disclosure in blood in an unstable angina patient group and a myocardial infarction patient group.

In the present disclosure, "LysoPC" is an abbreviation of lysophosphatidylcholine and PC stands for phosphatidylcholine.

Also, in the present disclosure, the expression "level" refers to the blood level of a biomarker and is used in the broadest sense, including objectively measured values of a biomarker included in blood, such as concentration, mass, etc. and the amount of the substance relative to another substance.

Hereinafter, the present disclosure is described in more detail.

In an aspect, the present disclosure provides a biomarker for diagnosing a cardiovascular disease, including one or more biological metabolite selected from lysophosphatidylcholine (LysoPC) (18:0), LysoPC (20:3), fatty acid (16:1) (palmitelaidic acid), fatty acid (18:0) (stearic acid), fatty acid (18:1) (oleic acid), fatty acid (18:2) (linoleic acid) and fatty acid (22:6) (docosahexaenoic acid). Specifically, the biological metabolites according to an exemplary embodiment of the present disclosure allow for not only the diagnosis of myocardial infarction among cardiovascular diseases but also the diagnosis of unstable angina occurring prior to the onset of myocardial infarction stage by stage.

Accordingly, in another aspect, the present disclosure provides a method for diagnosing a cardiovascular disease using the biomarker. Specifically, the present disclosure provides a method for diagnosing a cardiovascular disease, including: measuring the level of one or more biological metabolite selected from lysophosphatidylcholine (LysoPC) (18:0), LysoPC (20:3), fatty acid (16:1), fatty acid (18:0), fatty acid (18:1), fatty acid (18:2) and fatty acid (22:6) in blood taken from a subject; and comparing the level of the biological metabolite in the blood with the level of the biological metabolite in blood from a normal control group.

In an exemplary embodiment of the present disclosure, the level of the biological metabolite may be, for example, an objectively measured value of the biomarker included in blood, such as concentration, mass, etc., the amount of the substance relative to another substance, or the like.

In an exemplary embodiment of the present disclosure, the cardiovascular disease includes at least one of myocardial infarction and unstable angina occurring prior to the onset of the myocardial infarction. Specifically, the change in the level of LysoPC (18:0), LysoPC (20:3), fatty acid (16:1), fatty acid (18:0), fatty acid (18:1), fatty acid (18:2) and fatty acid (22:6) in blood may be different in myocardial infarction patients and unstable angina patients as compared to a normal control group. Also, the changes in the level of each of the seven biomarkers may be different each other in the same patients.

LysoPC is a phospholipid metabolite of the lipid metabolism occurring in cell membrane, blood, etc. and has a structure in which one of two fatty acids has been removed from phosphatidylcholine (PC) and only one fatty acid (R in Chemical Formula 1) is bound, as shown in Chemical Formula 1.

Chemical Formula 1

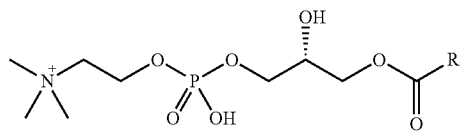

Among the biomarkers of the present disclosure, LysoPC (18:0) and LysoPC (20:3) refer to LysoPC wherein the numbers of carbon atoms and double bonds in the carbon chain are 18:0 and 20:3, respectively. Patients with cardiovascular diseases show different change in the concentration of the biomarkers depending on the numbers.

The fatty acid refers to a carboxylic acid of hydrocarbon chain having one carboxylic group (—COOH). It is degraded or synthesized in vivo through the fatty acid cycle. Like LysoPC, it is also represented by the numbers of carbon atoms and double bonds in the carbon chain. Among the biomarkers of the present disclosure, fatty acid (16:1), fatty acid (18:0), fatty acid (18:1), fatty acid (18:2) and fatty acid (22:6) refer to fatty acids wherein the numbers of carbon atoms and double bonds in the carbon chain are 16:1, 18:0, 18:1, 18:2 and 22:6, and they are respectively called palmitelaidic acid, stearic acid, oleic acid, linoleic acid and docosahexaenoic acid.

In an exemplary embodiment of the present disclosure, in the step of measuring the level of one or more biological metabolite selected from lysophosphatidylcholine (LysoPC) (18:0), LysoPC (20:3), fatty acid (16:1), fatty acid (18:0), fatty acid (18:1), fatty acid (18:2) and fatty acid (22:6) in blood taken from a subject, the subject may be a human or a non-human animal. In addition, although the LysoPC (18:0), LysoPC (20:3), fatty acid (16:1), fatty acid (18:0), fatty acid (18:1), fatty acid (18:2) and fatty acid (22:6) are taken from blood, they may also be taken from tissues other than blood without limitation.

The biomarkers according to an exemplary embodiment of the present disclosure have been explored from a metabolomic analysis of data obtained from the plasma of a normal control group and cardiovascular disease patient groups, specifically a myocardial infarction patient group and an unstable angina patient group. Since metabolomics elucidates the cause of various physiological changes occurring in vivo as a result from genetic differences and in response to physiological or environmental conditions by analyzing the composition and concentration of small-molecule metabolites in vivo, screening of biological metabolites based on metabolomics may allow for effective diagnosis of the change in metabolic pathways resulting from a cardiovascular disease in a subject.

In an exemplary embodiment of the present disclosure, the step of comparing the level of the biological metabolite may further include diagnosing that the subject has a cardiovascular disease if the level of at least one of LysoPC (20:3), fatty acid (16:1), fatty acid (18:1), fatty acid (18:2) and fatty acid (22:6) in the blood of the subject is higher as compared to the normal control group. In another exemplary embodiment of the present disclosure, the step of comparing the level of the biological metabolite may further include diagnosing that the subject has a cardiovascular disease if the level of at least one of LysoPC (18:0) and fatty acid (18:0) in the blood of the subject is lower as compared to the normal control group. Alternatively, the method may further include comparing the level of the seven biological metabolites in the blood at the same time. In an exemplary embodiment of the present disclosure, the normal control group refers to a group of healthy people without particular diseases.

In another aspect, the present disclosure provides a kit for diagnosing a cardiovascular disease, including a measuring unit measuring one or more biological metabolite selected from lysophosphatidylcholine (LysoPC) (18:0), LysoPC (20:3), fatty acid (16:1), fatty acid (18:0), fatty acid (18:1), fatty acid (18:2) and fatty acid (22:6).

In an exemplary embodiment of the present disclosure, the biological metabolite measuring unit of the diagnostic kit may include a substance, a detector, etc. capable of detecting one or more of the seven biological metabolites in blood. The detector is not particularly limited as long as it can measure or detect the level of the biological metabolites in blood. For example, a mass spectrometer, a nuclear magnetic resonance (NMR) spectrometer, a photodiode array (PDA), etc. may be used.

Also, the kit may further include an instruction including a method for diagnosing a cardiovascular disease. In an exemplary embodiment, since the cardiovascular disease includes at least one of myocardial infarction and unstable angina, the instruction may also include a method for diagnosing at least one of myocardial infarction and unstable angina.

Hereinafter, the present disclosure will be described in detail through test examples. However, the following test examples are for illustrative purposes only and it will be apparent to those of ordinary skill in the art that the scope of the present disclosure is not limited by the test examples.

Test Example 1

The following experiment was carried out in order to demonstrate the function of LysoPC (18:0), LysoPC (20:3), fatty acid (16:1), fatty acid (18:0), fatty acid (18:1), fatty acid (18:2) and fatty acid (22:6) according to an exemplary embodiment of the present disclosure as diagnostic biomarkers of myocardial infarction.

1. Selection of Test Subjects

Stable angina, unstable angina and myocardial infarction patients as patient groups and healthy people without such diseases as a normal control group were recruited for testing from Korea University Guro Hospital located in Seoul, Korea. The patient groups consisted of 72 stable angina patients, 23 unstable angina patients and 42 myocardial infarction patients, and the normal control group consisted of 40 healthy men and women without history of hypertension, diabetes, cardiovascular diseases, cerebrovascular diseases, chronic kidney disease, infectious diseases, etc. Both the patient groups and the control group were restricted in age to 45 years or older. It is because myocardial infarction or angina occurs mainly in middle-aged or elderly people rather than in the young and exhibits significant difference in those aged 45 years or older. By equally restricting the age of the patient groups and the control group, error in data interpretation that may occur due to difference in age was prevented.

2. Preparation of Standard Analyte Solution (Blood Sample)

Venous blood taken from the patient groups and the normal control group was collected in a sterilized plastic test tube surface-treated with an anticoagulant and was immediately centrifuged to obtain plasma samples. All the samples were kept at −80° C. prior to analysis. Then, the plasma sample was deproteinized by pretreating with methanol. Specifically, after the plasma sample was thawed to room temperature, ice-cold methanol of three volume equivalents was added. After completely mixing, centrifugation was performed and a portion of the supernatant was diluted by adding distilled water half (½) the volume of the supernatant.

3. Analysis of Biological Metabolites by Ultra High Performance Liquid Chromatography-Mass Spectrometry (UPLC-QTOF-MS)

The pretreated plasma samples of the patient groups and the normal control group were analyzed by ultra high performance liquid chromatography-quadrupole time-of-flight mass spectrometry (UPLC-QTOF-MS; ACQUITY UPLC system and Synapt G2 MS system, Waters).

Biological metabolites included in the plasma samples were separated by the ultra high performance liquid chromatography (UPLC) system according to their retention time and were detected by the Synapt G2 system according to their mass-to-charge ratio. Specifically, ACQUITY BEH $C_{18}$ (2.1×

100 mm, 1.7 μm) was used as a UPLC column in the UPLC system and the column temperature and the autosampler temperature were set to 50° C. and 4° C., respectively. As mobile phases, distilled water containing 0.1% formic acid (mobile phase A) and methanol containing 0.1% formic acid (mobile phase B) were used. A gradient elution was performed using a mixture of mobile phase A and mobile phase B at a flow rate of 0.4 mL/min. The order of injection was randomized to preclude any tendency resulting therefrom. Detection of the biological metabolites included in the plasma samples in the Synapt G2 system was performed in the positive and negative ionization modes of the mass spectrometer, respectively, and analyzed in the $MS^E$ mode.

A detailed analysis condition of the Synapt G2 system is as follows.

TABLE 1

| Acquisition mode | ESI (+/−) mode |
|---|---|
| Capillary voltage | (+) 3.2 kV/(−) 2.5 kV |
| Sample cone voltage | 40 V |
| Source temperature | 120° C. |
| Desolvation temperature | 350° C. |
| Cone gas flow | 100 L/h |
| Desolvation gas flow | 800 L/h |

Specifically, analysis was performed with the capillary voltage set at (+) 3.2 kV in the positive ionization mode and at (−) 2.5 kV in the negative ionization mode and the cone voltage set at 40 V using the electrospray ionization (ESI) method. The source temperature and the desolvation temperature were set to 120° C. and 350° C., respectively, and the cone gas flow rate and the desolvation gas flow rate were set to 100 L/h and 800 L/h, respectively. From the plasma analysis result by ultra high performance liquid chromatography-quadrupole time-of-flight mass spectrometry (UPLC-QTOF-MS), the analytical data of chromatograms and mass spectra were obtained.

4. Analysis of Concentration of Metabolites in Plasma Samples from Unstable Angina and Myocardial Infarction Patient Groups and Normal Control Group The analytical data of the metabolites included in the plasma samples obtained from the unstable angina and myocardial infarction patient groups and the normal control group were aligned using the MassLynx™ software (Waters) and the MarkerLynx™ software (Waters) to select candidate biomarkers exhibiting significant difference in the chromatograms and mass spectra. Specifically, the peak area of each candidate marker was adjusted and normalized by the peak area of the total ion chromatogram for reduction of data error between samples. Then, the normalized marker data were statistically analyzed using multivariate analysis by the orthogonal partial least square-discriminant analysis (OPLS-DA) method. FIG. 1 shows a result of the multivariate analysis. As seen from the score plot of FIG. 1, the data of the two groups are separated on either side of the y-axis, suggesting that the two groups show significant difference in markers.

Among the candidate markers that show difference in the two groups, the biomarkers exhibiting statistically significant difference were selected and their change in the normal group and the patient groups was analyzed. That is to say, the online databases such as the Human Metabolome Database (HMDB), the METLIN Metabolomics Database, etc. were used to identify the selected candidates and confirm the biomarkers relevant to myocardial infarction and unstable angina.

Figure 6:
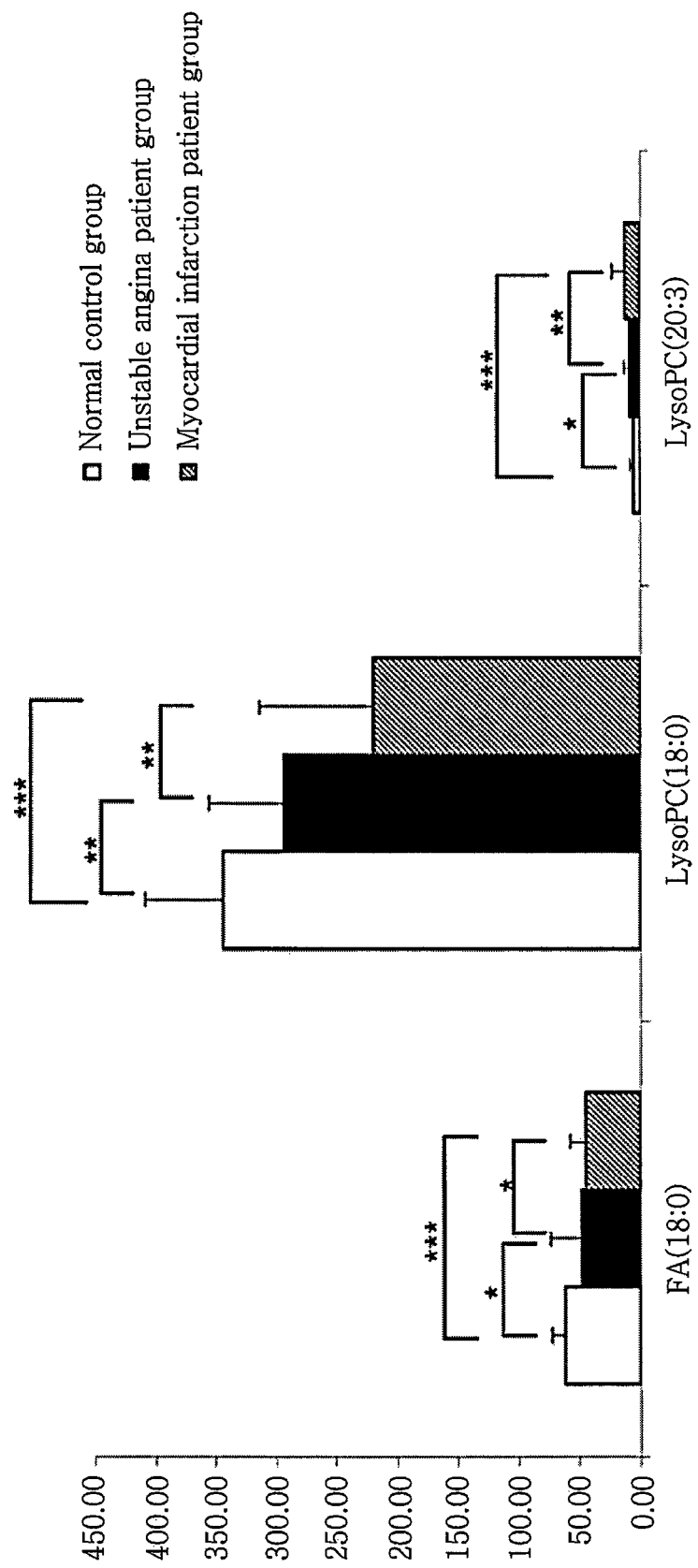
FIG. 6 compares the relative amount of LysoPC (18:0), LysoPC (20:3) and fatty acid (18:0) among metabolite biomarkers according to an exemplary embodiment of the present disclosure in blood in a normal control group, an unstable angina patient group and a myocardial infarction patient group.

The mean value of the relative amount of LysoPC (18:0), LysoPC (20:3), fatty acid (16:1), fatty acid (18:0), fatty acid (18:1), fatty acid (18:2) and fatty acid (22:6) as the biomarkers exhibiting statistically significant difference between the normal control group and the patient groups is shown in Table 2. The significant difference was tested by the Student's t-test. The level of the biomarkers in the plasma samples of the normal control group, the unstable angina patient group and the myocardial infarction patient group is shown in FIGS. 2-5. And, the level of fatty acid (18:0), LysoPC (18:0) and LysoPC (20:3) among them in the plasma samples of the unstable angina patient group and the myocardial infarction patient group is compared in FIG. 6. The mean values given in Table 2 are normalized peak area values.

TABLE 2

| | Normal control (NC) group | | Unstable angina (UA) patient group | | Myocardial infarction (MI) patient group | | P-value | | | |
|---|---|---|---|---|---|---|---|---|---|---|
| | | | | | | | NC group vs UA group | NC group vs MI group | UA group vs MI group | |
| Substance | Mean | S.D. | Mean | S.D. | Mean | S.D. | group | group | group | Change |
| FA (18:0) (stearic acid) | 62.27 | 10.18 | 49.11 | 24.12 | 45.81 | 11.86 | 0.012 | <0.001 | 0.043 | Decreased |
| LysoPC (18:0) | 345.23 | 64.35 | 293.66 | 63.20 | 220.88 | 92.98 | 0.003 | <0.001 | 0.001 | Decreased |
| LysoPC (20:3) | 5.60 | 2.34 | 8.62 | 5.33 | 13.38 | 9.36 | 0.016 | <0.001 | 0.010 | Increased |
| FA (16:1) (palmitelaidic acid) | 67.91 | 35.76 | 78.72 | 61.03 | 122.97 | 53.30 | 0.412 | <0.001 | 0.025 | Increased |
| FA (18:1) (oleic acid) | 236.88 | 86.34 | 270.14 | 188.16 | 481.05 | 207.46 | 0.396 | <0.001 | 0.001 | Increased |
| FA (18:2) (linoleic acid) | 223.74 | 63.43 | 230.44 | 119.97 | 349.67 | 109.17 | 0.791 | <0.001 | 0.002 | Increased |
| FA (22:6) (docosahexaenoic acid) | 168.41 | 62.00 | 183.57 | 130.79 | 268.52 | 101.46 | 0.578 | <0.001 | 0.037 | Increased |

As seen from Table 2, the myocardial infarction patient group exhibited significant increase in the amount of LysoPC (20:3), fatty acid (16:1), fatty acid (18:1), fatty acid (18:2) and fatty acid (22:6) and significant decrease in the amount of LysoPC (18:0) and fatty acid (18:0) as compared to the normal control group or the unstable angina patient group. This means that the seven substances can be utilized as biomarkers for specifically diagnosing myocardial infarction.

Also, among the biomarkers, LysoPC (18:0), LysoPC (20:3) and fatty acid (18:0) showed significant difference not only in the normal control group and the myocardial infarction patient group but also in the unstable angina patient group. This means that LysoPC (18:0), LysoPC (20:3) and fatty acid (18:0) can be utilized as biomarkers for identifying the progress of unstable angina and myocardial infarction.

Test Example 2

For further confirmation of the identification of LysoPC (18:0), LysoPC (20:3), fatty acid (16:1), fatty acid (18:0), fatty acid (18:1), fatty acid (18:2) and fatty acid (22:6), the biomarkers according to an exemplary embodiment of the present disclosure, as diagnostic biomarkers of myocardial infarction by stage, the same experiment as in the analysis of plasma samples in Test Example 1 was carried out using commercially available standard substances.

A comparative analysis result of LysoPC (18:0), fatty acid (16:1), fatty acid (18:0), fatty acid (18:1), fatty acid (18:2) and fatty acid (22:6) for the standard substances and the plasma samples of Test Example 1 is shown in Table 3.

TABLE 3

| Substances | m/z | Adduct | Retention time (min) Plasma sample | Retention time (min) Standard | Ratio of retention time relative to internal standard Plasma sample | Ratio of retention time relative to internal standard Standard |
|---|---|---|---|---|---|---|
| LysoPC (18:0) | 524.371 | $[M + H]^+$ | 10.84 | 11.09 | 2.00 | 2.02 |
| FA (16:1) (palmitelaidic acid) | 253.217 | $[M - H]^-$ | 10.17 | 10.33 | 1.89 | 1.89 |
| FA (22:6) (docosahexaenoic acid) | 327.233 | $[M - H]^-$ | 10.44 | 10.57 | 1.94 | 1.93 |
| FA (18:2) (linoleic acid) | 279.232 | $[M - H]^-$ | 10.60 | 10.71 | 1.97 | 1.95 |
| FA (18:1) (oleic acid) | 281.248 | $[M - H]^-$ | 11.25 | 11.38 | 2.09 | 2.08 |
| FA (18:0) (stearic acid) | 283.264 | $[M - H]^-$ | 11.96 | 12.1 | 2.22 | 2.20 |

As seen from Table 3, the plasma samples and the standard substances showed the same result in retention time and ratio of retention time relative to the internal standard, meaning that the biomarkers of the present disclosure are accurate.

Figure 7:
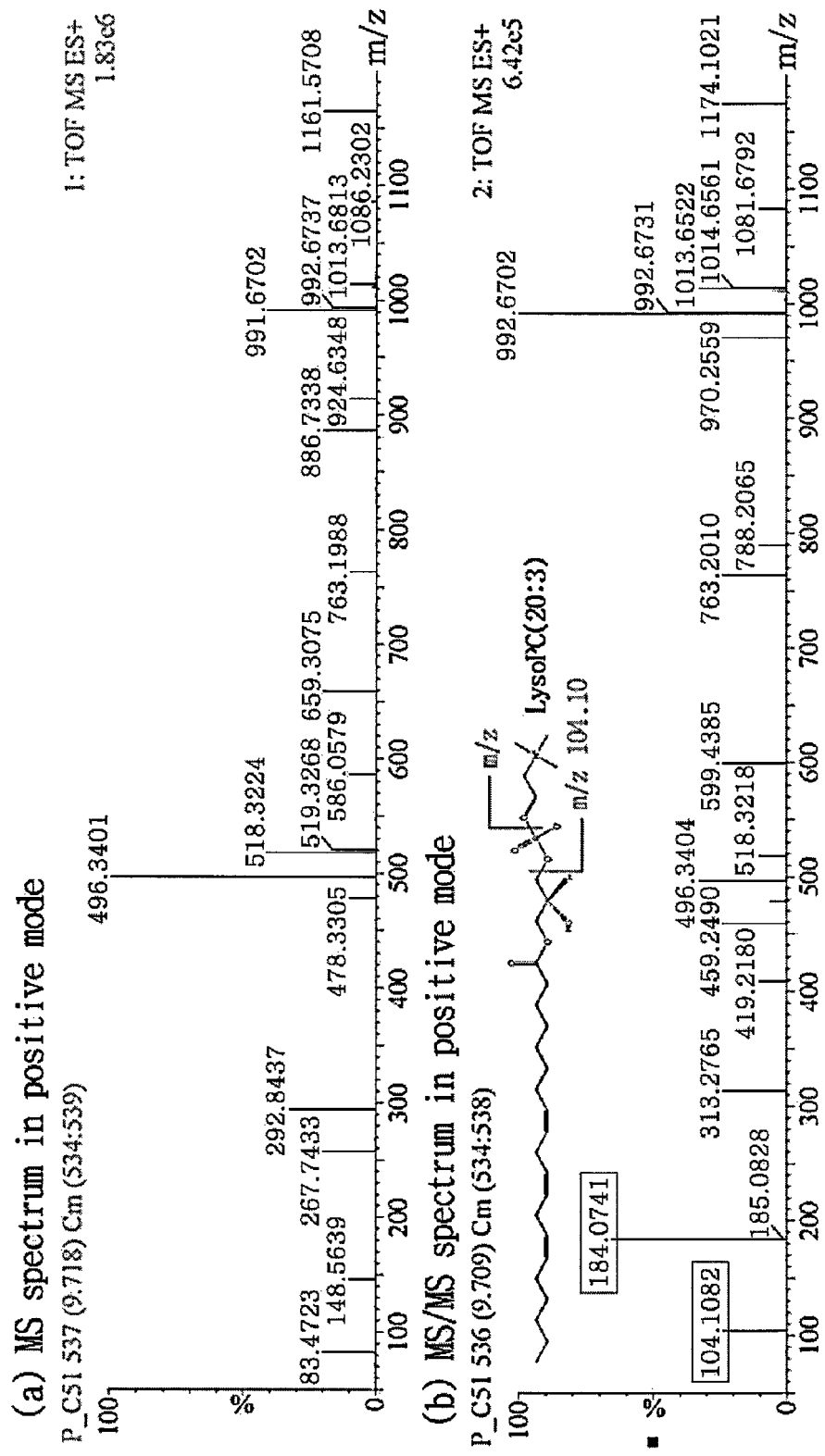
FIG. 7 compares the MS spectrum of LysoPC (20:3) among metabolite biomarkers according to an exemplary embodiment of the present disclosure obtained in Test Example 1 with a theoretical spectrum pattern available from an online database [The spectra (a) and (b) of FIG. 7 were obtained in the positive ionization mode. The spectrum pattern of LysoPC (20:3) obtained from the database is shown in FIG. 7 (b) together with the structure of LysoPC (20:3).]
Figure 8A:
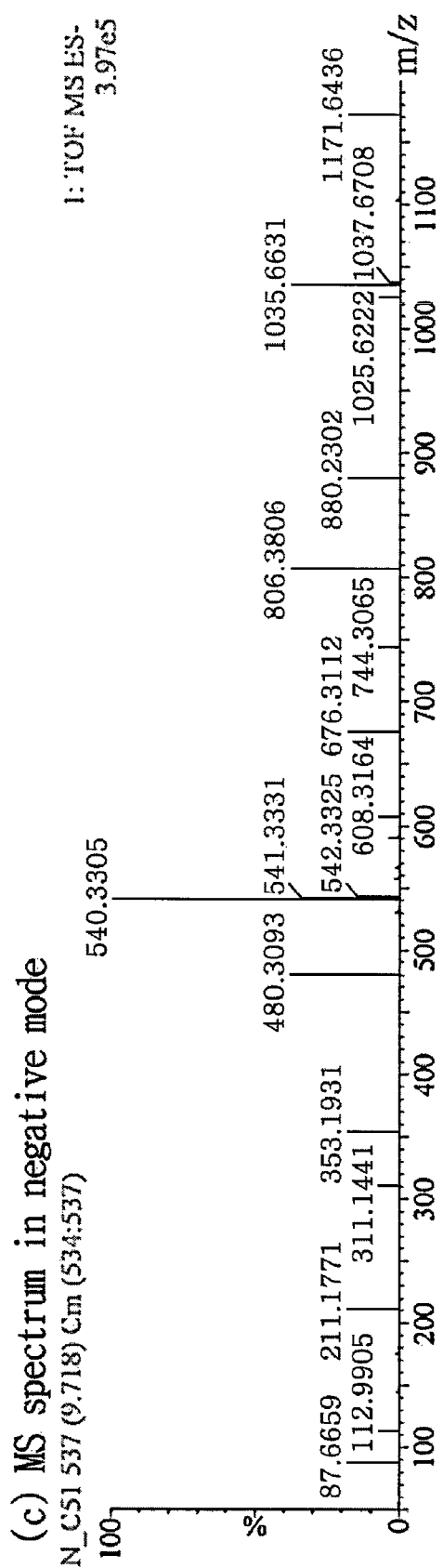
Figure 8B:
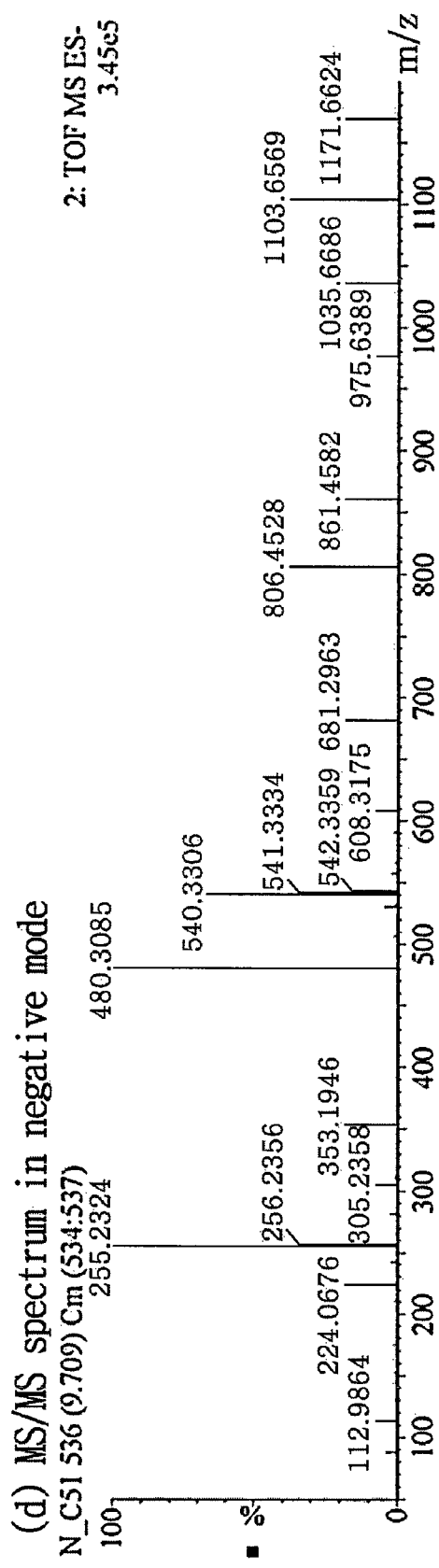
Figure 8C:
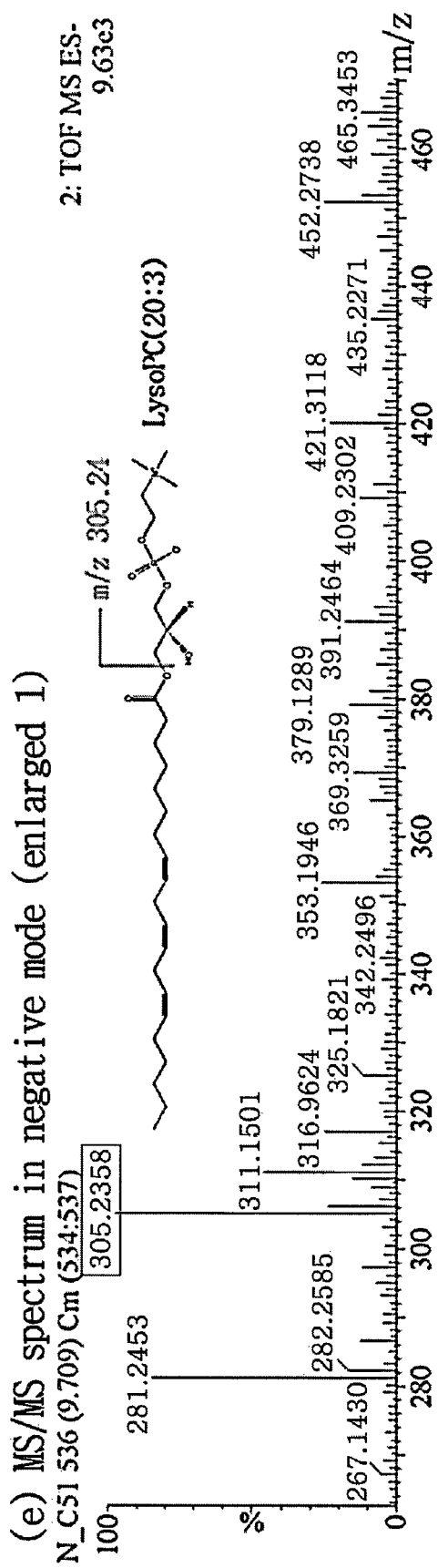

Since no standard substance was commercially available for LysoPC (20:3), the theoretical spectrum pattern available from online databases [Human Metabolome Database (http://www.hmdb.ca/) and METLIN (http://metlin.scripps.edu/index.php)] were compared with the spectrum obtained in Test Example 1. The MS/MS spectrum pattern of LysoPC (20:3) obtained from the databases is shown in (b) of FIG. 7 and (e) (f) of FIGS. 8C and 8D together with the structure of LysoPC (20:3). Since the spectrum pattern obtained from the online databases matches with the spectrum of LysoPC (20:3) obtained in Test Example 1, it can be seen that the biomarker of the present disclosure is accurate.

While the exemplary embodiments have been shown and described, it will be understood by those skilled in the art that various changes in form and details may be made thereto without departing from the spirit and scope of the present disclosure as defined by the appended claims.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:
1. A method for diagnosing a cardiovascular disease in a subject, comprising:
   obtaining a plasma sample from a patient subject from a normal subject by centrifugation of venous blood sample taken from the patient subject and the normal subject and incubating said plasma sample for a period of time;
   deproteinizing the plasma sample by pretreating with methanol;
   measuring a level of one or more biological metabolites selected from the group consisting of lysophosphatidylcholine (LysoPC) (18:0), LysoPC (20:3), fatty acid (16:1), fatty acid (18:0), fatty acid (18:1), fatty acid (18:2) and fatty acid (22:6) in said plasma sample;
   wherein the measuring the level of one or more biological metabolites comprises separating the biological metabolites by an ultra-high performance liquid chromatography system and detecting said metabolites using a mass spectrometer;
   comparing the level of the biological metabolites in the plasma sample of the patient subject with the level of the biological metabolites in the plasma sample of the normal subject;
   wherein the level of the biological metabolites in the plasma samples is a measurable concentration of said biological metabolites in the plasma samples;
   wherein the comparing the level of the biological metabolites further comprises diagnosing that the subject has a cardiovascular disease if the level of at least one of LysoPC (20:3), fatty acid (16:1), fatty acid (18:1), fatty acid (18:2) and fatty acid (22:6) in the plasma sample of the patient subject is higher as compared to the level in the plasma sample of the normal subject;
   wherein the comparing the level of the biological metabolites further comprises diagnosing that the subject has a cardiovascular disease if the level of at least one of LysoPC (18:0) and fatty acid (18:0) in the plasma sample of the patient subject is lower as compared to the level in the plasma sample of the normal subject; and
   identifying a progress of myocardial infarction and unstable angina occurring prior to an onset of the myo- cardial infarction in the patient subject based on the level of the biological metabolites in the plasma sample of the patient subject.

2. The method for diagnosing a cardiovascular disease in a subject according to claim 1 further comprising comparing the level of all of said biological metabolites in the plasma samples at the same time.

\* \* \* \* \*